(12) United States Patent
Fago et al.

(10) Patent No.: US 8,012,124 B1
(45) Date of Patent: Sep. 6, 2011

(54) FRONT LOADED MEDICAL FLUID SYRINGE MOUNTING

(75) Inventors: Frank M. Fago, Mason, OH (US); Robert Ziemba, Cincinnati, OH (US); Gary S. Wagner, Taylor Mill, KY (US)

(73) Assignee: Liebel-Flarsheim Company LLC, Cincinnati, OH (US)

( * ) Notice: Subject to any disclaimer, the term of this patent is extended or adjusted under 35 U.S.C. 154(b) by 151 days.

(21) Appl. No.: 12/035,293

(22) Filed: Feb. 21, 2008

Related U.S. Application Data

(60) Division of application No. 10/386,957, filed on Mar. 12, 2003, which is a division of application No. 09/665,374, filed on Sep. 20, 2000, now Pat. No. 6,569,127, which is a continuation of application No. 08/896,695, filed on Jul. 18, 1997, now abandoned.

(51) Int. Cl.
*A61M 1/00* (2006.01)

(52) U.S. Cl. ........................................ 604/151; 604/131

(58) Field of Classification Search .......... 604/151–155, 604/131, 218, 221, 222, 239, 201; 600/431–435; 128/DIG. 1, DIG. 12
See application file for complete search history.

(56) References Cited

U.S. PATENT DOCUMENTS

| | | | |
|---|---|---|---|
| 4,342,312 A | 8/1982 | Whitney et al. | |
| 4,465,473 A | 8/1984 | Rueegg | |
| 5,279,569 A | 1/1994 | Neer et al. | |
| 5,300,031 A | 4/1994 | Neer et al. | |
| 5,383,858 A | 1/1995 | Reilly et al. | |
| 5,520,653 A | 5/1996 | Reilly et al. | |
| 5,779,675 A * | 7/1998 | Reilly et al. | 604/131 |
| 5,899,885 A | 5/1999 | Reilly et al. | |
| 6,368,307 B1 | 4/2002 | Ziemba et al. | |
| 6,569,127 B1 | 5/2003 | Fago et al. | |

FOREIGN PATENT DOCUMENTS

| | | |
|---|---|---|
| WO | 97 07841 A | 3/1997 |
| WO | 97 36635 A | 10/1997 |

\* cited by examiner

*Primary Examiner* — Theodore Stigell
*Assistant Examiner* — Laura Schell
(74) *Attorney, Agent, or Firm* — Wood, Herron & Evans, LLP

(57) ABSTRACT

Various sealing structures are used in a front-loading injector, for preventing leakage of spilled fluid from an external surface of a syringe into the vicinity of the drive ram. For example, a sealing gasket may be incorporated into the front face of the injector housing, for mating to the rearward circular edge of the cylindrical body of a syringe. Alternatively, sealing and locking functions may be performed by a single structure on the rearward end of the syringe. Further, leakage may be prevented by including a non-planar sealing flange on the syringe, positioned on the syringe forward of the locking structure, or by a two-piece structure, including a syringe and a separate leakage stopping washer for surrounding the syringe to halt the flow of fluid along the exterior of the syringe. As part of this aspect, or as an independent feature, the syringe may include an annularly discontinuous flange forward of the locking structure, for providing mechanical support for the syringe against the injector. Alternatively, an iris-like structure may be incorporated into the front surface of the injector, for closing about the syringe upon insertion of the syringe into the injector.

31 Claims, 6 Drawing Sheets

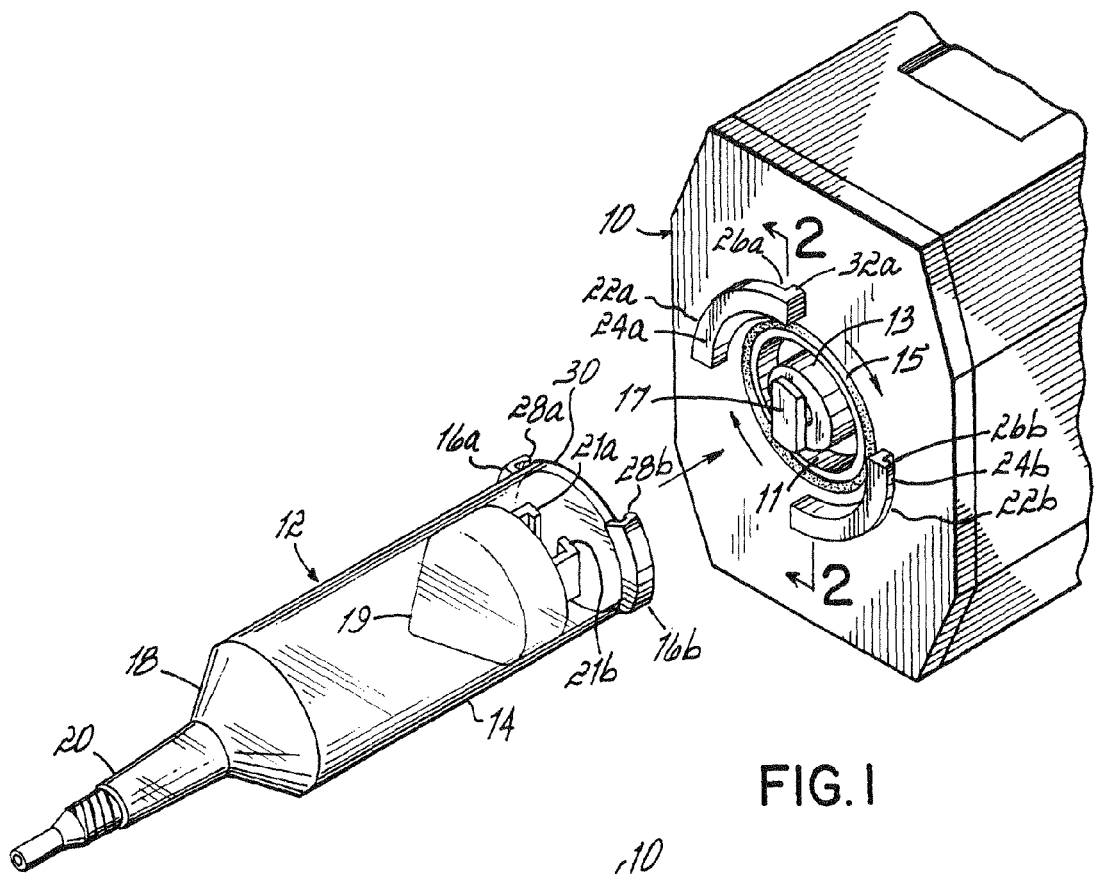
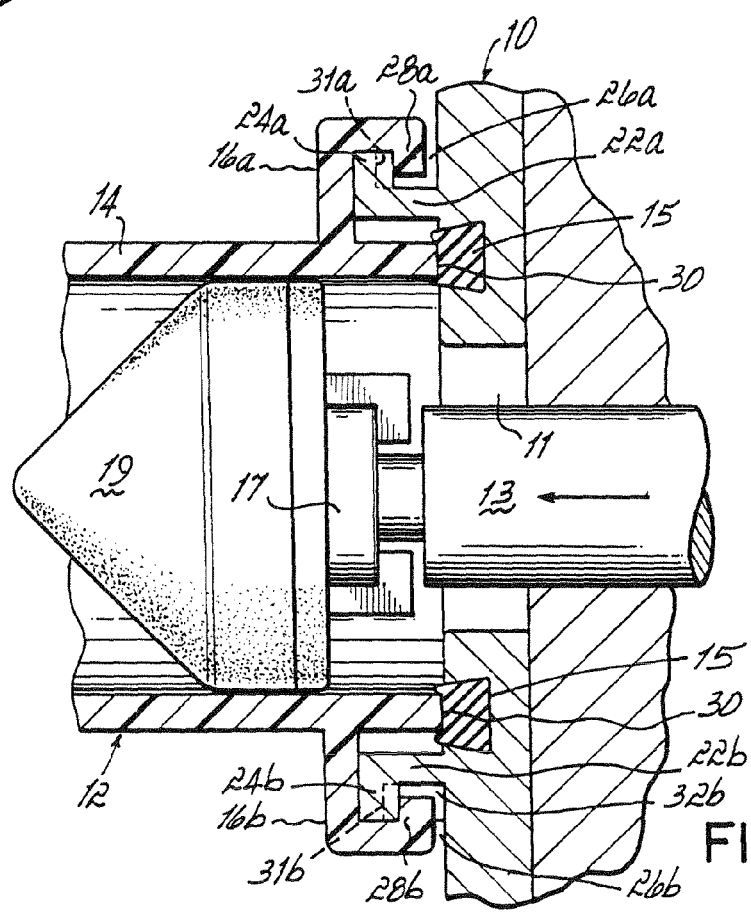
FIG. 1
FIG. 2

FRONT LOADED MEDICAL FLUID SYRINGE MOUNTING

CROSS REFERENCE TO RELATED APPLICATIONS

This application is a division of U.S. patent application Ser. No. 10/386,957 filed 12 Mar. 2003, which is a division of U.S. Pat. No. 6,569,127, filed 20 Sep. 2000, which is a continuation of now abandoned U.S. patent application Ser. No. 08/896,695 filed 18 Jul. 1997, the entire disclosures of which are hereby incorporated by reference.

Further, this application is related to U.S. patent application Ser. No. 11/458,463 filed 19 Jul. 2006, and co-pending U.S. patent application Ser. No. 11/420,664 filed 26 May 2006, which claims the same priority as above.

Further, this application is related to U.S. patent application Ser. No. 11/677,946 filed 22 Feb. 2007, and U.S. patent application Ser. No. 11/677,926, filed 22 Feb. 2007, which claims the same priority as above.

Further, this application is related to U.S. patent application Ser. No. 11/738,925, filed Apr. 23, 2007, which claims the same priority as above.

FIELD OF THE INVENTION

The present invention relates to medical fluid injectors for injecting medical fluid into patients.

BACKGROUND OF THE INVENTION

Injectors are devices that expel fluid, such as contrast media, from a syringe and through a tube into an animal. An injector often includes an injector unit, usually adjustably fixed to a stand or support, which has a drive ram that couples to the plunger of a syringe to drive the plunger forward to expel fluid into the tube, or to drive the plunger rearward to draw fluid into the syringe to fill it. Usually the syringe is disposable.

U.S. Pat. No. 5,300,031, which is assigned to the same assignee as this application, discloses a front-loading injector, and is incorporated by reference herein in its entirety. This injector has a pressure jacket mounted to its front face for receiving a syringe. A syringe having an open back end is inserted into the pressure jacket, and an umbrella surface on the front of the syringe, is coupled to the pressure jacket by a rotating motion. This same rotating motion causes the plunger in the syringe to couple to the end of the ram. The pressure jacket supports the side walls of the syringe against injection pressure during operation of the injector. After an injection, a reverse rotating motion unlocks the syringe from the pressure jacket and releases the plunger from the ram, so the syringe can be removed and replaced.

A second front-loading injector structure is disclosed in U.S. Pat. No. 5,383,858, which is also incorporated by reference herein in its entirety. This front loading injector structure is similar in many respects to that disclosed in U.S. Pat. No. 5,300,031, with the main difference that the injector of the primary figures (FIGS. 1-8) of U.S. Pat. No. 5,383,858, does not include a pressure jacket on the front surface thereof. Rather, the syringe is made of a hard plastic material which is deemed sufficiently self-supporting to withstand injection pressures. In the front-loading injector of U.S. Pat. No. 5,383,858, the syringe and injector, and the plunger and ram, are connected to each other by a single twisting motion, and disconnected from each other by a reverse twisting motion; thus, the connection and disconnection procedures are similar to that used by the injector of U.S. Pat. No. 5,383,858.

Both of the above-noted U.S. Patents show syringes incorporating locking structures for locking the syringe to the front surface of the injector, as well as a disc-like, annular sealing flange for contacting and sealing to an annular edge on the front surface of the injector or its pressure jacket. This annular sealing flange prevents contrast media or any other injectable fluid which might flow along the outside of the syringe, from leaking into the area where the ram exits the injector, and potentially fouling the mechanical systems inside of the injector.

SUMMARY OF THE INVENTION

There are several disadvantages to including an annular disc-like sealing flange on the syringe. This disc-like flange can be difficult to mold, and when molded to a sufficient thinness to permit a sealing, interference fit with the front face of the injector, can be fragile and subject to breakage. Accordingly, there is a need for a front-loading injector and syringe which does not require the inclusion of a disc-like sealing flange on the syringe.

In accordance with a first aspect of the present invention, this need is met by an injector including an annular, sealing gasket incorporated into the front face of the injector housing, for mating to the rearward circular edge of the cylindrical body of a syringe. A locking structure on the outer surface of the syringe and the face of the injector, holds the syringe in tight sealing contact with the gasket on the face of the injector, preventing leakage from the outside surfaces of the syringe into the vicinity of the drive mechanism of the injector.

In specific disclosed embodiments of this aspect of the invention, the locking structure on the outer surface of the syringe comprises one or more radially extending members, which mate to one or more radially extending members on the face of the injector. The members on the face of the injector may be radially disposed tabs, for receiving flanges on an outer surface of the syringe. The flanges on the syringe are rotated into and out of engagement with the tabs on the face of the injector. The tabs on the injector may form a radially outwardly-facing groove, for receiving a radially inwardly-facing flange on the syringe, or alternatively, the tabs on the injector may have a radially inwardly-facing groove, for receiving a radially outwardly-facing flange on the syringe.

In a second specific embodiment, the face of the injector may include a slot, for receiving the radially-outwardly extending members on the syringe, by sliding the syringe transversely to its axis, into engagement with the injector. As a third alternative, the face of the injector may include a rotating turret, for engaging radially-outwardly extending members on the syringe, and rotating the syringe transversely relative to its axis, into registration with the drive mechanism on the injector.

In accordance with a second aspect of the present invention, the sealing function is provided by incorporating sealing and locking functions into a single structure on the rearward end of the syringe. Specifically, the end of the syringe includes a radially outwardly-extending sealing structure, which includes integral locking members for engaging mating structures on the face of the injector.

In specific disclosed embodiments of this aspect, these locking members form a channel in the sealing structure on the syringe, for receiving tabs on an interior surface of the injector housing, so that the sealing structure may be inserted into the housing and rotated to lock the syringe to the injector.

In accordance with another aspect of the present invention, leakage is prevented by including a non-planar sealing flange on the syringe, positioned on the syringe forward of the locking structure. In specific embodiments of this aspect, the non-planar sealing flange includes a cusp feature for diverting fluid flowing along the surface of the syringe.

In yet another aspect of the present invention, leakage is prevented by a two-piece structure, including a syringe and a separate leakage stopping washer for surrounding the syringe to halt the flow of fluid along the exterior of the syringe.

A separate unique feature of this aspect of the invention, is the structure of the syringe, which includes an annularly discontinuous flange forward of the locking structure, for providing mechanical support for the syringe against the injector. This discontinuous flange not only provides mechanical support for the syringe when mounted to the injector, but also aids in positioning the leakage stopping washer, which when installed abuts against the annularly discontinuous flange.

In accordance with another aspect of the present invention, leakage is prevented by an iris-like structure on the front surface of the injector. The iris-like structure includes mechanical actuators for closing the iris-like structure about the syringe upon insertion of the syringe into the injector, thus forming a seal between the syringe and injector.

In specific embodiments of this aspect, the mechanical actuators interact with locking flanges on the rearward surface of the syringe, for translating the iris-like structure into engagement of the syringe upon rotation of the locking flanges on the syringe into the mechanical actuators.

The above and other objects and advantages of the present invention shall be made apparent from the accompanying drawings and the description thereof.

BRIEF DESCRIPTION OF THE DRAWINGS

The accompanying drawings, which are incorporated in and constitute a part of this specification, illustrate embodiments of the invention and, together with a general description of the invention given above, and the detailed description of the embodiments given below, serve to explain the principles of the invention.

FIG. 1 is a perspective view of a first embodiment of a syringe and a replacement face plate for the injector described in U.S. Pat. No. 5,383,858;

FIG. 2 is a cross-sectional view taken on line 2-2 of FIG. 1, of the syringe and injector of FIG. 1 when coupled together;

DETAILED DESCRIPTION OF SPECIFIC EMBODIMENTS

Figure 3:
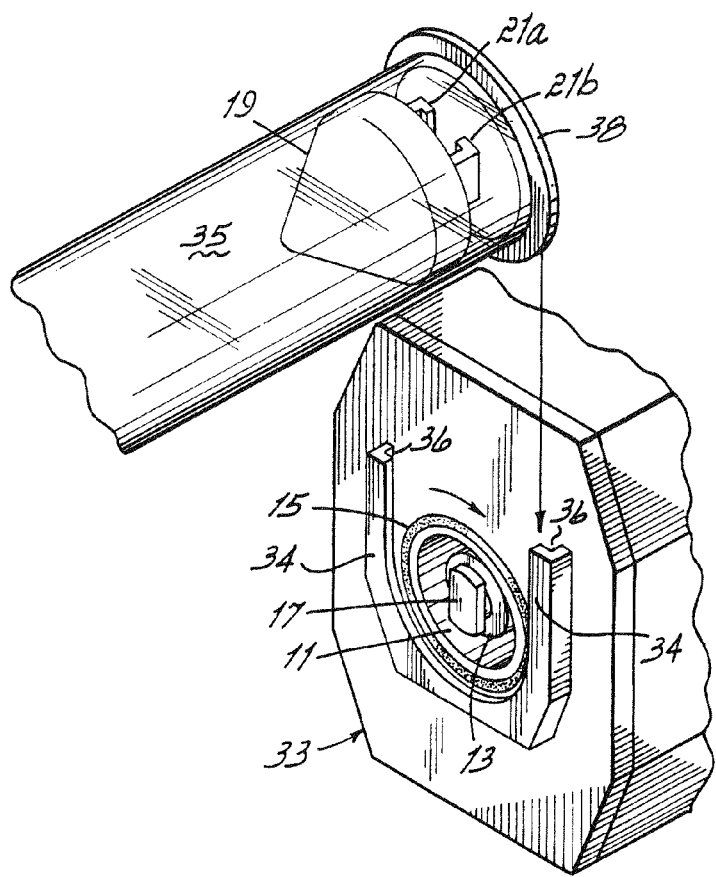
FIG. 3 is a perspective view of a second embodiment of a syringe and a replacement face plate for the injector described in U.S. Pat. No. 5,383,858.

Referring now to FIG. 1, in accordance with a first embodiment of the present invention, the injector disclosed in U.S. Pat. No. 5,383,858 is outfitted with a replacement face plate 10, incorporating features for mounting a syringe 12. Face plate 10 includes an opening 11 at a central location thereof. The syringe drive ram 13 of the injector extends through opening 11 to engage the plunger of a syringe mounted to face plate 10, by a relative rotational motion of the plunger and ram, in the manner described in U.S. Pat. No. 5,383,858. Surrounding opening 11 is a circular gasket 15 of a flexible material such as rubber.

The structure of syringe 12 is notable in that it does not include a disc-like sealing flange on its exterior. Rather, the exterior surface of cylindrical barrel 14 of the syringe is smooth but for two locking flanges 16a and 16b extending from the rearward end of the syringe. The syringe also includes, as is conventional, a plunger 19 sealingly engaging an interior of cylindrical barrel 14 and sliding within barrel 14 between an open rearward end of barrel 14 and a closed forward end 18. Forward end 18 terminates in a discharge extension 20, to which tubing is mounted to carry injected fluid to a patient. A rearward surface of plunger 19 includes flanges 21a and 21b similar to those described in U.S. Pat. No. 5,383,858, for engaging head 17 of plunger drive ram 13.

Flanges 16a and 16b on syringe 12 are matable to locking structures 22a and 22b, respectively, on the front face of face plate 10. Specifically, face plate 10 includes radially outwardly-extending tabs 24a and 24b, which form radially outwardly-facing grooves 26a and 26b which extend partially annularly about opening 11 in face plate 10. Locking flanges 16a and 16b on the rearward end of syringe 12, include radially inwardly-extending tabs 28a and 28b positioned to interlock into grooves 26a and 26b behind tabs 24a and 24b.

Referring now to FIGS. 1 and 2, in this embodiment, a syringe is installed onto injector by first translating the syringe along its axis in the orientation shown in FIG. 1, until the rearward circular edge 30 of cylindrical barrel 14 of the syringe, engages gasket 15 surrounding opening 11 in face plate 10. Then, syringe 12 is rotated clockwise to guide tabs 28a and 28b on the rearward end of syringe 12 into grooves 26a and 26b on face plate 10. When syringe 12 is rotated ninety degrees clockwise, tab 28a engages stop 32a at the end of groove 26a, thus preventing further clockwise rotation of syringe 12. (Another stop 32b, is incorporated at the clockwise end of groove 26b.) Thus, when installing a syringe, the syringe is rotated clockwise for approximately ninety degrees until further rotation is impossible, at which point the user can be certain that the syringe is fully installed.

To facilitate installation of a syringe to face plate 10, the diameter of locking structures 22a and 22b may be slightly reduced at their counter-clockwise ends, to facilitate mating of the syringe locking structures 16a and 16b to flanges 22a and 22b on face plate 10. In addition, the thickness of tabs 24a and 24b may be reduced at their counter-clockwise ends (e.g., to the thickness shown in hidden lines at 31a and 31b), to facilitate mating of the syringe locking structures to tabs 24a and 24b and to tighten the rearward circular edge 30 of syringe 12 against gasket 15 as the syringe is rotated clockwise into position. Furthermore, small buttons and detents, or other features, may be incorporated into locking structures 16a and 16b and/or flanges 22a and 22b, placed so as to interact and provide audible and/or tactile feedback to a user installing a syringe onto face plate 10, so the user knows when the syringe is properly positioned.

As is visible in FIG. 2 in particular, ninety-degree rotation of syringe 12 into engagement with face plate 10, also causes flanges 21a and 21b on plunger 19 to engage head 17 on plunger drive ram 13, so that plunger drive ram 13 can thereafter drive plunger 19 forward and rearward within the cylindrical barrel 14 of the syringe, to perform an injection.

Also visible in FIG. 2, is the interaction of the rearward surface 30 of syringe 12, and gasket 15. When syringe 12 is fully installed to face plate 10, gasket 15 is partially compressed against rearward surface 30 of syringe 12, so as to form a seal therewith. This seal reduces leakage of injection fluid from the exterior surface of the barrel 14 of syringe 12, into the area where drive ram 13 exits from face plate 10. This gasket provides the functions provided by the disc-shaped sealing flange described in the above-noted U.S. Patents, without requiring complex manufacturing or involving breakable parts.

It will be appreciated that alternative forms of locking structure may be used to mount syringe 12 to face plate 10. For example, tabs 24a, 24b on the face plate 10 may form an inwardly-facing groove such as the groove (23s) shown in the main figures (FIGS. 1-8) of U.S. Pat. No. 5,383,858 in particular, for mounting to outwardly-projecting structures on syringe 12. In one specific embodiment, the outwardly-projecting locking structures 16a and 16b on the rearward end of syringe 12 are sized so as to be insertable into the inwardly-facing groove 23s of the injector described in U.S. Pat. No. 5,383,858, so that syringe 12 may be mounted without modification to the injector of U.S. Pat. No. 5,383,858, or may be mounted to the substitute face plate 10 shown in FIGS. 1 and 2.

Referring now to FIG. 3, a third alternative locking structure can be described. In this alternative, a replacement face plate 33 includes radially inwardly-extending tabs 34 which form an inwardly-facing slot 36 for gripping locking structure on the rearward end of the syringe 12. In this embodiment, syringe 35 may be mounted by sliding the syringe transversely to its axis, into slot 36 and engagement with tabs 34. The locking structure on the rearward end of syringe 35 may include a number of tabs such as are shown in FIGS. 1 and 2, or may be a continuous, annular flange 38 such as is shown in FIG. 3.

It will be appreciated that the face plate 33 shown in FIG. 3 includes a gasket 15 identical in function and placement to the gasket 15 discussed above with reference to FIGS. 1 and 2. Gasket 15 forms a seal with the rearward surface of syringe 35, to form a seal therewith to inhibit the flow of fluid from the exterior of syringe 35 into the region surrounding plunger drive ram 13.

In the embodiment of FIG. 3, flanges 21a and 21b on plunger 19 are similar to those described above and in U.S. Pat. No. 5,383,858, and are coupled to head 17 of plunger drive ram 13 by rotating syringe 12 after syringe 12 has been fully inserted into slot 36 on face plate 33. Other coupling structures could also be used, including, for example, a disk-shaped end on drive ram 13, for engaging flanges 21a and 21b upon lateral translation of syringe 35 into slot 36 on face plate 33, without requiring rotation.

It will be appreciated that keyed features might be included into slot 36 and/or flange 38 to require that syringe 35 be placed in a proper rotational orientation before syringe 35 can be slid into slot 36. For example, the opening of slot 36 may be slightly narrower than the widest diameter of flange 38, and flange 38 might include a flat which must be oriented properly for flange 38 to pass through the narrowed opening of slot 36 and into a mounted position.

Figure 4:
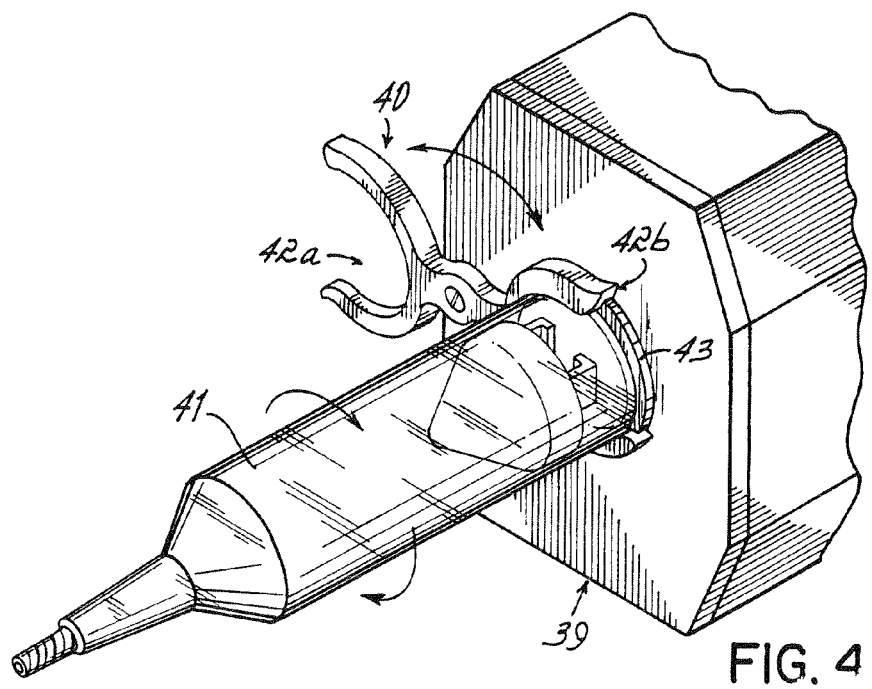
FIG. 4 is a perspective view of a third embodiment of a syringe and a replacement face plate for the injector described in U.S. Pat. No. 5,383,858.

Referring now to FIG. 4, a second alternative structure for mounting a syringe to an injector is shown. In this alternative, face plate 39 incorporates a turret 40. Turret 40 includes two jaws 42a and 42b into which one or two syringes can be inserted. The syringe 41 is similar to the syringe shown in FIG. 3, in that it includes a continuous, annular flange 43 at its rearward end. As before, a gasket (not shown) is incorporated into face plate 39, surrounding the opening through which the plunger drive ram emerges from the injector, so that the rearward surface of syringe 41 forms a seal therewith to inhibit leakage of spilled fluid into the internal mechanisms of the injector.

Figure 5:
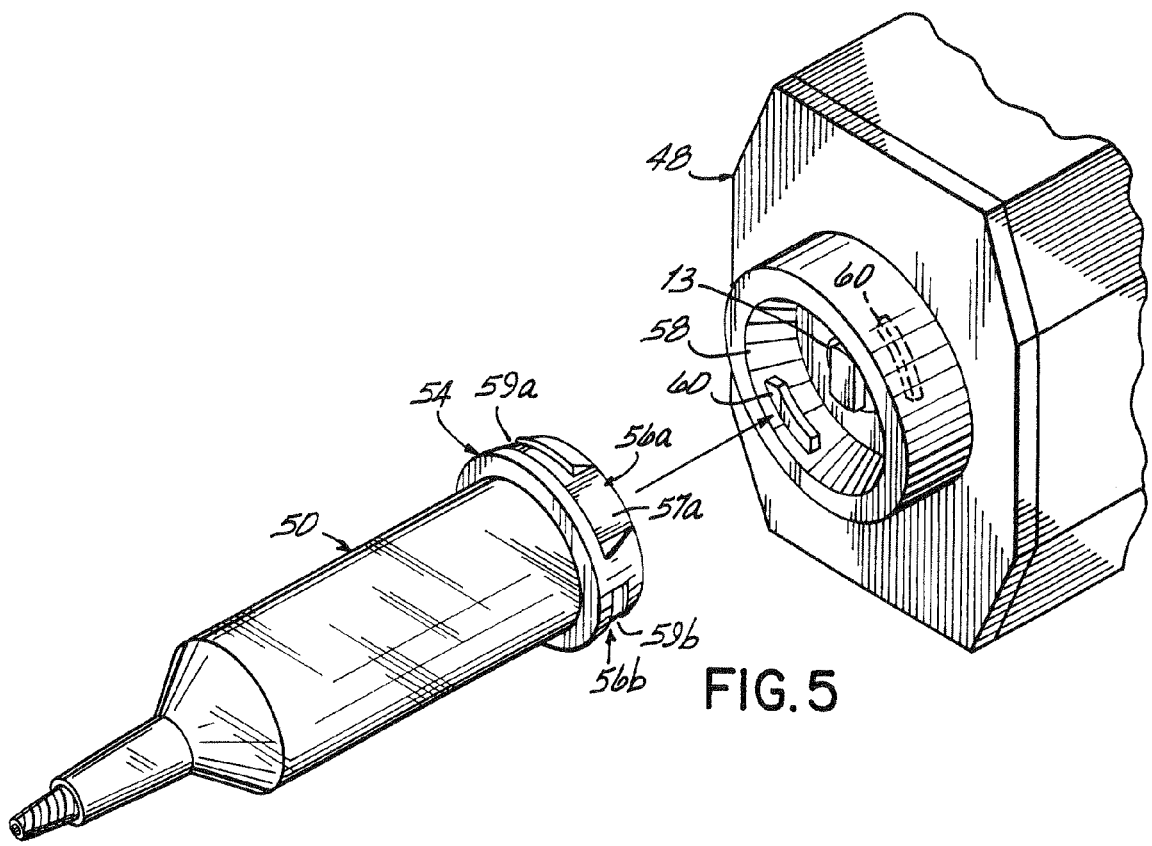
FIG. 5 is a perspective view of a fourth embodiment of a syringe and replacement face plate for the injector described in U.S. Pat. No. 5,383,858.

Referring now to FIG. 5, a second type of syringe-injector sealing structure can be discussed. The injector has a replacement face plate 48, for mounting a syringe 50. Syringe 50 includes a single-piece, combination locking and sealing structure 54 at its rearward end. Structure 54, which has a conically-shaped outer surface, has two channels 56a and 56b molded therein. Each channel 56a and 56b includes an axial opening portion (57a in channel 56a, not shown in channel 56b) and an annular portion (59a in channel 56a, 59b in channel 56b). Face plate 48 includes a conically-shaped opening 58 surrounding injector drive ram 13, which is matable to the conically-shaped outer surface of structure 54 on the rearward end of syringe 50. Within opening 58 are tabs 60 positioned annularly about an interior of opening 58 and sized to fit into the axial opening portions of channels 56a and 56b of syringe structure 54. A gasket (not shown) may also be incorporated into the rim of opening 58 forward of tabs 60 for sealing purposes.

Syringe 50 is installed into injector face plate 48 by inserting structure 54 at the rearward end of syringe 50 into opening 58, with tabs 60 aligned with the axial opening portions of channels 56a and 56b, and then rotating syringe 50 clockwise over an angle of approximately ninety degrees, thus locking tabs 60 into the annular portions 59a and 59b of channels 56a and 56b. Once locked to face plate 48, a seal is formed between syringe 50 and face plate 48 which inhibits flow of spilled fluid from the exterior of syringe 50 into the mechanism of drive ram 13.

Figures 6, 7:
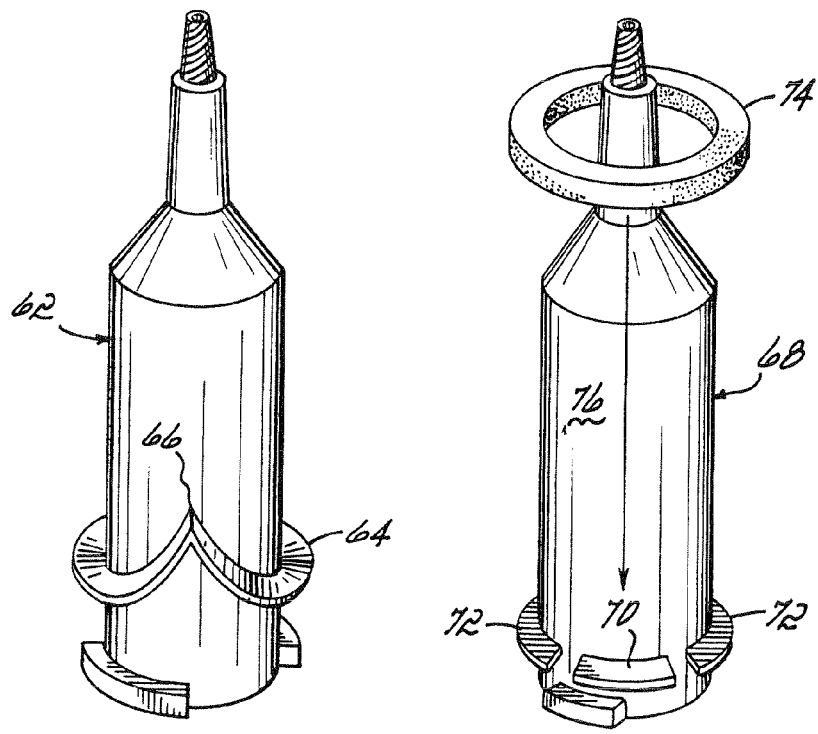
FIG. 6 is a perspective view of a fifth embodiment of a replacement syringe for the injector described in U.S. Pat. No. 5,383,858.
FIG. 7 is a perspective view of a sixth embodiment of a replacement syringe for the injector described in U.S. Pat. No. 5,383,858.

Referring now to FIG. 6, in accordance with a further embodiment of the present invention, a syringe such as that shown in U.S. Pat. No. 5,383,858 can be improved by enhancing the rigidity of the sealing flange. Specifically, the sealing flange can be made non-planar, e.g., as shown in FIG. 6, the sealing flange 64 may be formed with a cusp-shaped feature 66, thus enhancing the rigidity of the flange while continuing to guide spilled fluid flowing rearwardly along the exterior of the syringe away from the drive mechanism. The non-planar sealing flange shown in FIG. 6 thus provides the leakage protection function of the planar flange shown in U.S. Pat. No. 5,383,858. U.S. Pat. No. 5,383,858 further indicates that the sealing flange described in that patent stabilizes the syringe while mounted to the injector. This function is also provided by the sealing flange 62 shown in FIG. 6 in that there are substantial annular portions of sealing flange 62 which contact the sealing rim on the injector shown in U.S. Pat. No. 5,383,858, lending the needed stability.

Referring now to FIG. 7, in accordance with a further embodiment, a syringe 68 for mounting to the injector described in U.S. Pat. No. 5,383,858, includes an annular sealing flange which is annularly discontinuous, i.e., separated into segments such as 70. An annularly discontinuous flange, while not necessarily accomplishing the sealing function described in U.S. Pat. No. 5,383,858, does provide stability for the mounted syringe, in that segments 70 contact and form an interference fit with the face of the injector. (The placement of segment 70, and additional segments 72, can be determined based on the stability needed.) Furthermore, the annularly discontinuous segments 70, can perhaps be made of more thick layers of plastic, since the gaps between the segments make the segments more able to flex than an annularly continuous flange. Moreover, an annular flange formed in segments may be more easily molded than an annularly continuous flange.

To provide a sealing function, particularly in connection with syringes having an annularly discontinuous sealing flange, but also in other applications, a leakage stopping washer 74 may be provided in conjunction with the syringe. Washer 74 may be formed of solid rubber, sponge rubber, paper or any other absorbent and/or sealing material. Washer 74 may be disposable, and sold with syringe 68 for one-time use, or may be reusable. In either case, washer 74 is slipped over the cylindrical barrel 76 of syringe 68. Washer 74 is made of an elastic material and is formed with a slight interference fit relative to the cylindrical barrel 76 of syringe 68, so that washer 74 forms a seal with barrel 76 to inhibit leakage past washer 74. In one embodiment, flange segments 70 are used to position washer 74 at the rearward end of syringe 68 so that washer 74 is opposite to the face of the injector when syringe 68 is installed on the injector. In other embodiments, washer 74 may be positioned at any other location along the cylindrical barrel 76 of syringe 68.

Figure 8:
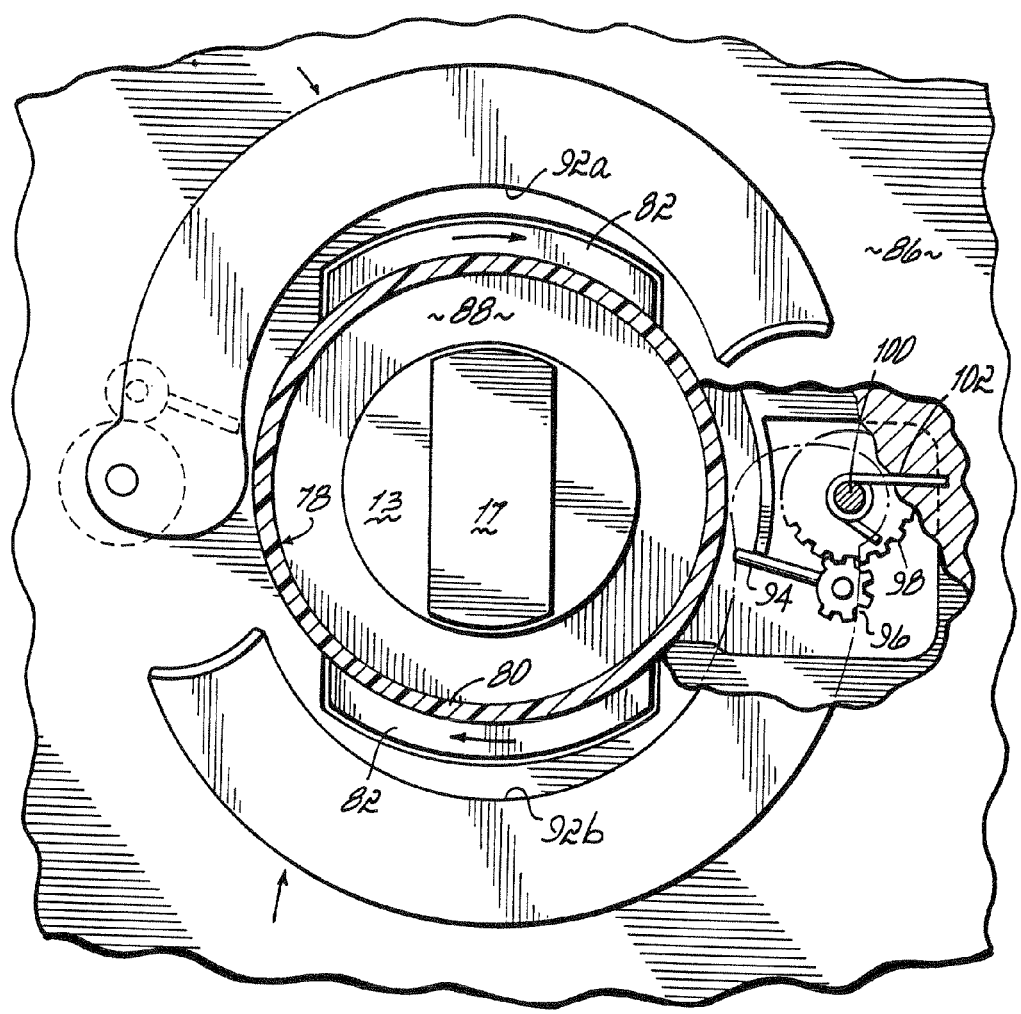
FIG. 8 is partial cut-away front view of a seventh embodiment of a replacement face plate for the injector described in U.S. Pat. No. 5,383,858, showing a sealing mechanism in an open position for receiving a syringe.

Referring to FIG. 8, in accordance with a further embodiment, a sealing function may be provided by an iris-like structure on a face plate of the injector, for closing about the syringe to provide a seal between the face plate and outer barrel of the syringe. As seen in FIG. 8, the syringe 78 includes a cylindrical barrel 80, and locking flanges 82 projecting from barrel 80 adjacent a rearward end of the syringe. Thus, the structure of the syringe is similar to that of the syringe shown in U.S. Pat. No. 5,383,858, with the annular sealing flange removed.

The syringe 78 is mounted into an opening in a replacement face plate 86 mounted on the front face of the injector. An opening 88 in the face plate permits the plunger drive ram 13, and in particular the plunger-mounting head 17 thereof, to emerge from the injector and engage and drive the plunger within the syringe. Face plate 86 further includes annular grooves of the kind illustrated in U.S. Pat. No. 5,383,858, so that locking flanges 82 of a syringe may be inserted into the face plate 86 in the orientation shown in FIG. 8, and then rotated into a locked position on the face plate.

As seen in FIG. 8, in addition to the structures described above, face plate 86 includes two sealing arms 90a and 90b which, in the open position illustrated in FIG. 8, permit locking flanges 82 of a syringe to pass into the face plate for locking to the face plate. Sealing arms 90a and 90b are arcuate sections, having an inside radius of curvature along edges 92a and 92b which is approximately equal to the radius of the cylindrical wall 80 of the syringe 78.

Figure 9:
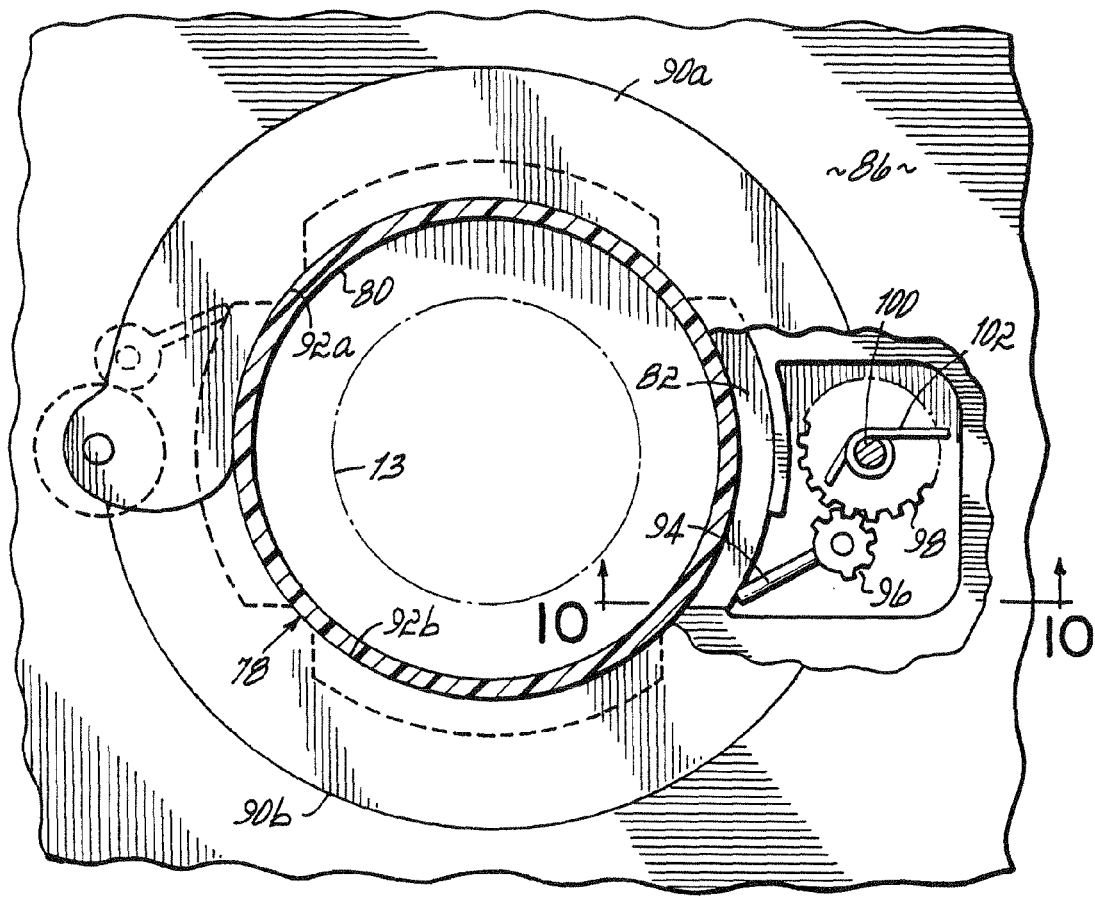
FIG. 9 is a view similar to FIG. 8, showing the sealing mechanism in a closed position as a result of a syringe being mounted thereto.

Referring now to FIGS. 8 and 9, the motion of sealing arms 90a and 90b from their open position of FIG. 8 to their closed position of FIG. 9 can be illustrated. Specifically, when a syringe is inserted into face plate 86 in the orientation shown in FIG. 8, and then turned clockwise to the orientation shown in FIG. 9, this rotational motion causes sealing arms 90a and 90b to similarly rotate clockwise from the open positions shown in FIG. 8 into the closed positions shown in FIG. 9. As can be seen in FIG. 9, in their closed positions the interior edges 92a and 92b of sealing arms 90a and 90b engage the outer cylindrical wall 80 of the syringe and form a seal therewith, thus inhibiting leakage of spilled fluid along the wall of the syringe. (The interior edges 92a and 92b of sealing arms 90a and 90b may carry rubber or other flexible seals such as are shown at edges 92a and 92b illustrated in FIG. 10.) At the same time sealing arms 90a and 90b lend mechanical stability to the syringe when it is mounted on the injector face plate 86.

Figure 10:
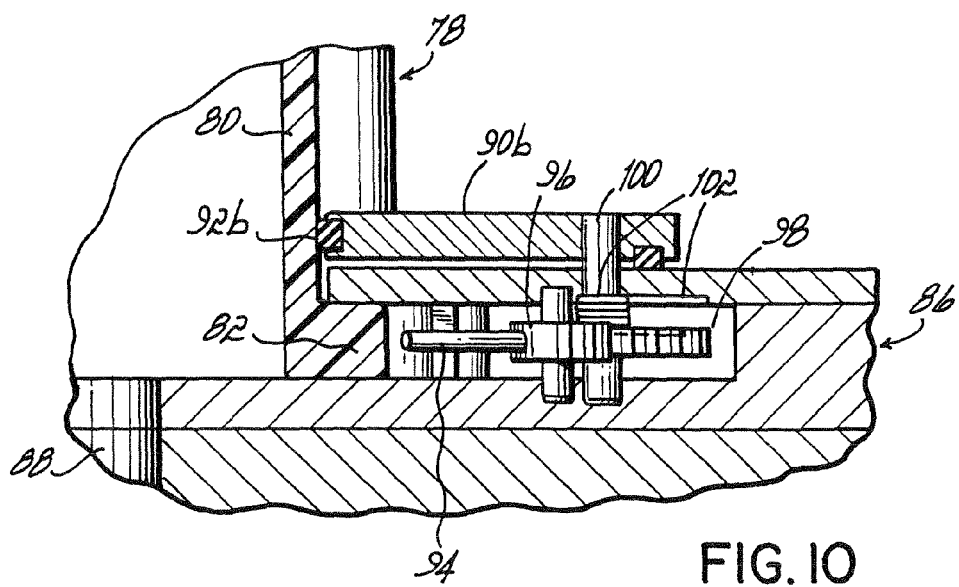
FIG. 10 is a cross-sectional view taken on line 10-10 of FIG. 8, of the actuating mechanism incorporated in the face plate of FIGS. 8 and 9.

Now referring to FIGS. 8, 9 and 10, in the illustrated embodiment, rotation of arms 90a and 90b is generated through mechanical mechanisms including a lever arm 94, which drives a pinion gear 96, which meshes with a main gear 98 rotationally coupled to the sealing arm 90. Clockwise rotation of the syringe from the position shown in FIG. 8 to the position shown in FIG. 9, causes locking flange 82 of the syringe to engage and rotate lever arm 94 counterclockwise. Counterclockwise motion of lever arm 94 causes counterclockwise motion of pinion gear 96. Pinion gear 96, meshing with main gear 98, causes main gear 98 to rotate clockwise, driving the connected sealing arm to rotate clockwise to its closed position.

As shown in FIG. 10, main gear 98 is rotationally locked to a shaft 100, which passes through face plate 86 and into sealing arm. Thus, rotation of main gear 98 causes rotation of shaft 100 and corresponding rotation of sealing arm 90b. A torsion spring 102 coupled between main gear 98 and face plate 86 produces a return force tending to rotate main gear 98, shaft 100 and sealing arm 90 counterclockwise to an open position whenever the syringe is rotated counterclockwise toward its disengaged position.

Figure 11:
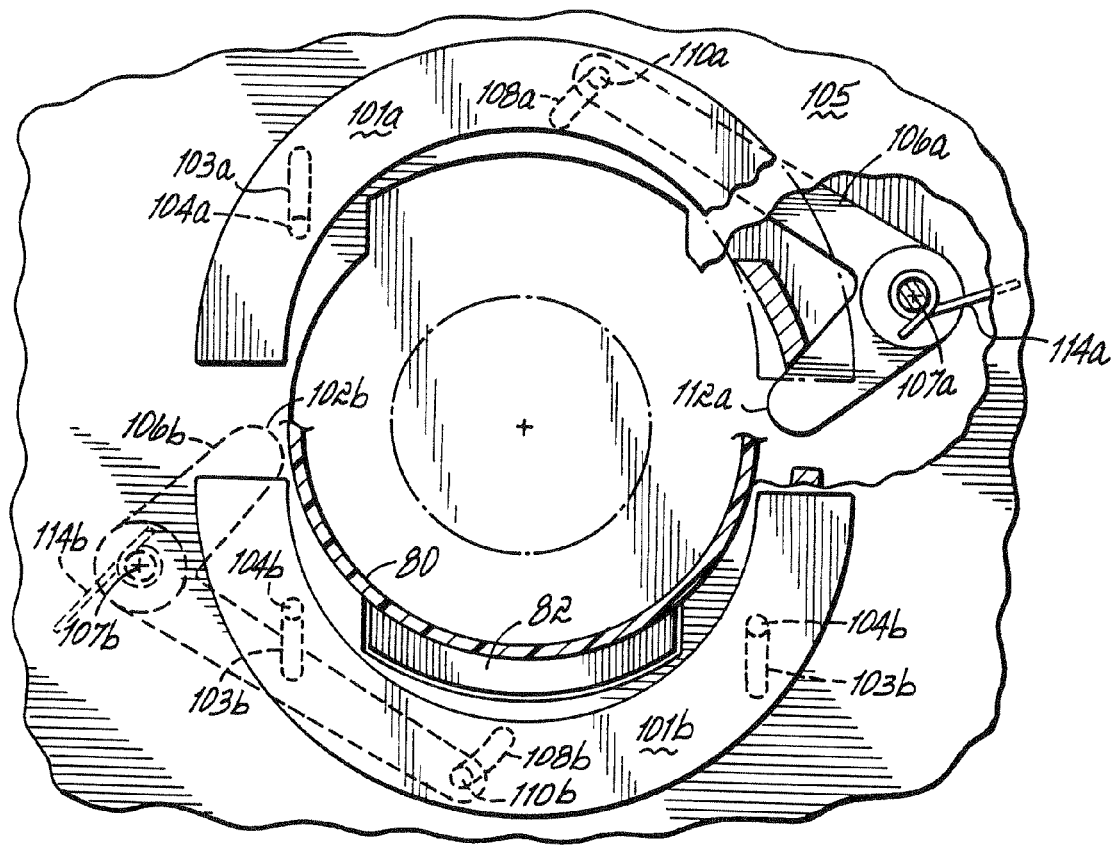
FIG. 11 is a partial cut-away front view of an eighth embodiment of a replacement face plate for the injector described in U.S. Pat. No. 5,383,858, showing a sealing mechanism in an open position for receiving a syringe.
Figure 12:
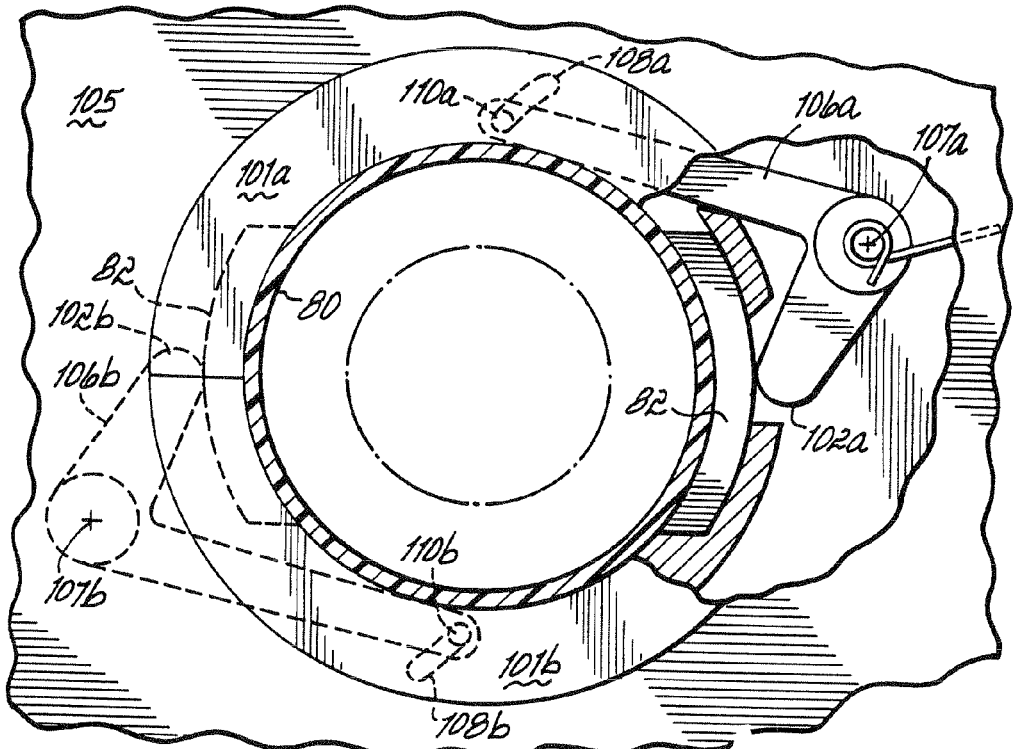
FIG. 12 is a view similar to FIG. 11, showing the sealing mechanism in a closed position as a result of a syringe being mounted thereto.

Referring to FIGS. 11 and 12, in an alternative embodiment, sealing arms 101a and 101b translate laterally between their open and closed positions, to provide a sealing function when a syringe is installed to the injector. The syringe used in this embodiment is similar to that used in the embodiment of FIGS. 8, 9 and 10. However, sealing arms 101a and 101b are different in structure. Sealing arms 101a and 101b include, on their rearward faces, channels 103a and 103b, for receiving pins 104a and 104b on the face plate 105 of the injector. Sealing arms 101a and 101b translate laterally with respect to the axis of the syringe, such that pins 104a and 104b slide within channels 103a and 103b, guiding the motion of arms 101a and 101b. Motion is imparted to sealing arms 101a and 101b by lever arms 106a and 106b, respectively, which pivot about axes 107a and 107b, respectively. Lever arms 106a and 106b include pins 110a and 110b at their exterior ends, which are received into channels 108a and 108b on the rearward faces of sealing arms 101a and 101b. Counterclockwise rotation of lever arms 106a and 106b causes pins 110a and 100b to interact with channels 108a and 108b to drive sealing arms 101a and 101b to the closed positions shown in FIG. 12. Clockwise rotation of lever arms 106a and 106b causes pins 110a and 100b to interact with channels 108a and 108b to drive sealing aims 101a and 101b to the open positions shown in FIG. 11.

Insertion and rotation of a syringe into a locked position in face plate 105, causes rotation of lever arms 106a and 106b to close sealing arms 101a and 101b. Specifically, a syringe is inserted with locking flanges 82 in the positions shown in FIG. 11. Next, the syringe barrel 80 is rotated clockwise approximately ninety degrees, from the orientation shown in FIG. 11 to the orientation shown in FIG. 12. This rotation causes locking flanges 82 to engage ends 112*a* and 112*b* of sealing arms 101*a* and 101*b*, causing counterclockwise rotation of levers 106*a* and 106*b* about axes 107*a* and 107*b*, thus bringing sealing arms 101*a* and 101*b* to their closed positions shown in FIG. 12.

Counterclockwise rotation of the syringe to unlock it from face plate 105, opens sealing arms 101*a* and 101*b* to permit the syringe to be removed. Specifically, torsion springs such as 114*a* and 114*b* on each lever 106*a* and 106*b*, exert a force upon levers 106*a* and 106*b* to urge levers 106*a* and 106*b* to rotate clockwise. Thus, when the syringe is rotated so that locking flanges 82 no longer interact with ends 112*a* and 112*b* of levers 106*a* and 106*b*, levers 106*a* and 106*b* rotate clockwise, opening sealing arms 101*a* and 101*b* to the positions shown in FIG. 11, so that the syringe may be removed.

While the present invention has been illustrated by a description of various embodiments and while these embodiments have been described in considerable detail, it is not the intention of the applicants to restrict or in any way limit the scope of the appended claims to such detail. Additional advantages and modifications will readily appear to those skilled in the art. The invention in its broader aspects is therefore not limited to the specific details, representative apparatus and method, and illustrative example shown and described. Accordingly, departures may be made from such details without departing from the spirit or scope of applicant's general inventive concept.

What is claimed is:

1. A front-loading injector for injecting fluid from a syringe having a barrel, a closed forward end with a discharge opening therein, an open rearward end, and structure extending radially outward from and integrally included on the barrel, wherein the structure is located toward a rearward end of the barrel, the injector comprising:
   an injector housing having a front with an opening therein and an injection ram in the injector housing extendable along an axis of the ram through the opening to drive a plunger in a syringe mounted to the injector;
   a member moveable relative to an axis between a retracted position and an engaged position in which the member engages the syringe forward of the structure on the syringe; and
   a cam coupled to the member, the cam interacting with the structure on the syringe such that rotation of the syringe actuates the cam, the cam causing movement of the member upon cam actuation.

2. The front-loading injector of claim 1 further comprising:
   a second member moveable relative to an axis between a retracted position and an engaged position in which the second member engages the syringe forward of the structure on the syringe; and
   a second cam coupled to the second member, the second cam interacting with the structure on the syringe such that rotation of the syringe actuates the second cam, the second cam causing radial movement of the second member upon actuation of the second cam.

3. The front-loading injector of claim 2 wherein each member includes a syringe engaging surface which, when the respective member is in its engaged position, extends in an arc more than 90 degrees around the barrel of the syringe.

4. The front-loading injector of claim 1 wherein the member includes an arcuate surface which, when the member is in its engaged position, extends in an arc more than 90 degrees around the barrel of the syringe.

5. The front-loading injector of claim 1 wherein a surface of the member has a fixed arcuate shape conforming approximately to an exterior of the barrel of the syringe.

6. The front-loading injector of claim 1 wherein:
   the member is movable radially relative to an axis of the syringe; and
   the injector includes an actuator, mounted on the housing and linked to the cam and member, which is operable to move the member radially into and out of engagement with the barrel of the syringe.

7. The front-loading injector of claim 1 wherein:
   the member comprises an arm having a syringe engaging surface, the arm being mounted to the injector about a pivot axis spaced from an axis of the syringe, wherein the arm pivots about the pivot axis to move the member and the syringe engaging surface thereof between the retracted and engaged positions.

8. The front-loading injector of claim 1 wherein:
   the member has a slot defined therein; and
   the cam includes a pin linked to the member to move in the slot of the member to actuate the member between the retracted and engaged positions.

9. The front-loading injector of claim 1 wherein the member comprises a sealing surface for forming a seal with the barrel of the syringe.

10. The front-loading injector of claim 1 wherein the barrel of the syringe is cylindrical.

11. The front-loading injector of claim 1 wherein the structure on the syringe comprises radially extending and annularly discontinuous flanges at the rearward end of the syringe, and the injector comprises at least one annular groove for receiving the flanges by insertion and rotation of the flanges into the at least one annular groove.

12. The front-loading injector of claim 1 wherein the barrel of the syringe is devoid of a disc-like, annular sealing flange designed to contact and form a seal with the injector.

13. The front-loading injector of claim 1 wherein the barrel of the syringe is devoid of a disc-like, annular sealing flange designed to contact and form a seal with a face plate of the injector.

14. The front-loading injector of claim 1 wherein the member and cam are incorporated into a face plate of the injector.

15. The front-loading injector of claim 1 wherein the structure on the syringe is annularly discontinuous.

16. The front-loading injector of claim 15 wherein the cam interacts with the annular discontinuity in the structure to cause movement of the member.

17. A medical fluid injection assembly comprising:
   an injector housing having an opening defined therein;
   a syringe that includes:
      a cylindrical barrel having an open rearward end, a closed forward end, a discharge opening defined in the closed forward end, and a structure projecting radially outward from an exterior of and located toward a rearward end of the barrel, wherein the structure is located within the injector housing; and
      a plunger disposed within and movable relative to the barrel; and
   a drive ram extendable along an axis thereof through the opening in the injector housing to drive the plunger of the syringe relative to the barrel of the syringe;
   a member that is moveable relative to the axis of the drive ram between:
      an engaged position in which the member engages the barrel of the syringe forward of the structure; and a retracted position in which the at least a portion of the barrel that includes the structure may be removed from within the injector housing; and a cam coupled to the member, wherein the cam interacts with the structure of the syringe such that rotation of the syringe actuates the cam, the cam causing movement of the member upon cam actuation.

18. The injection assembly of claim 17 further comprising a second member that is moveable relative to the axis of the drive ram between:

an engaged position in which the second member engages the barrel of the syringe forward of the structure; and a retracted position in which the syringe may be removed from the opening; and a second cam coupled to the second member, wherein the second cam interacts with the structure of the syringe such that rotation of the syringe actuates the second cam, the second cam causing movement of the second member upon cam actuation.

19. The injection assembly of claim 18 wherein each member includes a syringe engaging surface which, when the respective member is in its engaged position, projects in an arc more than 90 degrees around the barrel of the syringe.

20. The injection assembly of claim 17 wherein the member includes an arcuate surface which, when the member is in its engaged position, extends in an arc more than 90 degrees around the barrel of the syringe.

21. The injection assembly of claim 17 wherein a surface of the member has a fixed arcuate shape with a radius of curvature approximately equal to an exterior of the barrel of the syringe.

22. The injection assembly of claim 17 wherein:

the member is movable radially relative to an axis of the syringe; and the injector includes an actuator, mounted on the housing and linked to the cam and member, which is operable to move the member radially into and out of engagement with the barrel of the syringe.

23. The injection assembly of claim 17 wherein the member comprises an arm having a syringe engaging surface, the arm being mounted to the injector about a pivot axis spaced from an axis of the syringe, wherein the arm pivots about the pivot axis to move the member and the syringe engaging surface thereof between the retracted and engaged positions.

24. The injection assembly of claim 17 wherein:

the member has a slot defined therein; and the cam includes a pin linked to the member to move in the slot of the member to actuate the member between the retracted and engaged positions.

25. The injection assembly of claim 17 wherein the member comprises a sealing surface for forming a seal with the barrel of the syringe.

26. The injection assembly of claim 17 wherein the structure of the syringe comprises radially projecting and annularly discontinuous flanges at the rearward end of the syringe, and the injector comprises at least one annular groove for receiving the flanges by insertion and rotation of the flanges into the at least one annular groove.

27. The injection assembly of claim 17 wherein the syringe is devoid of a disc-like, annular sealing flange designed to contact and form a seal with the injector.

28. The injection assembly of claim 17 wherein the syringe is devoid of a disc-like, annular sealing flange designed to contact and form a seal with a face plate of the injector.

29. The injection assembly of claim 17 wherein the member and cam are incorporated into a face plate of the injector.

30. The injection assembly of claim 17 wherein the structure of the syringe is annularly discontinuous.

31. The injection assembly of claim 30 wherein the cam interacts with the annular discontinuity of the structure to cause movement of the member.

* * * * *